US00PP33483P3

(12) United States Plant Patent
Casano

(10) Patent No.: US PP33,483 P3
(45) Date of Patent: Sep. 14, 2021

(54) ***CANNABIS* PLANT NAMED 'DIVINA'**

(50) Latin Name: *Cannabis sativa L.*
Varietal Denomination: Divina

(71) Applicant: Phytoplant Research S.L., Córdoba (ES)

(72) Inventor: Salvatore Casano, Cordova (ES)

(73) Assignee: PHYTOPLANT RESEARCH S.L., Cordova (ES)

( * ) Notice: Subject to any disclaimer, the term of this patent is extended or adjusted under 35 U.S.C. 154(b) by 0 days.

(21) Appl. No.: 16/350,538

(22) Filed: Nov. 28, 2018

(65) Prior Publication Data

US 2020/0170162 P1 May 28, 2020

(51) Int. Cl.
*A01H 5/02* (2018.01)
*A01H 6/28* (2018.01)
*A61K 36/185* (2006.01)

(52) U.S. Cl.
USPC ..... Plt./258
CPC ..... *A01H 6/28* (2018.05); *A61K 36/185* (2013.01)

(58) Field of Classification Search
USPC ..... Plt./258, 263.1
CPC ... A01H 5/00; A01H 5/12; A01H 6/28; A01H 5/02; A61K 36/185; G06F 3/0481; G06T 2207/00
See application file for complete search history.

(56) References Cited

U.S. PATENT DOCUMENTS

PP27,475 P2 12/2016 Kubby

OTHER PUBLICATIONS

Upov Pluto Plant Variety Database 20191001, retrieved on Oct. 1, 2019, retrieved from the Internet at https://www.upov.int/pluto/en/index.jsp, one page. (Year: 2019).*
Behe, B., et al.; (1999), Consumer Preferences for *Geranium* Flower Color, Leaf Variegation, and Price. HortScience 34, 740-742.
Casano, S., and Grassi, G. (2009). Valutazione di terreni di coltura per la propagazione in vitrodella canapa (*Cannabis sativa* L.). Italus Hortus 16, 109-112.
Casano, S. (2019). Development of ornamental Cannabis sativa L. cultivars: phytochemical, morphological, genetic characterization and propagation aspects. Acta Hortic. 1263, 283-290 https://doi.org/10.17660/ActaHortic.2019.126337.
Cheniclet, C., and Carde, J.P. (1985). Presence of leucoplasts in secretory cells and of monoterpenes in the essential oil: a correlative study. Journal of Botany 34, 219-238.
Codesido, V., et al. (2020). Cannabinoids and terpenoids yields of the ornamental *Cannabis sativa* L. cultivar 'Divina' characterized by a variegated foliage as morphological marker. Acta Hortic. 1287, 161-168 https://doi.org/10.17660/ActaHortic.2020.1287.21.
de Meijer, et al.; (2003). The inheritance of chemical phenotype in *Cannabis sativa* L. Genetics 163, 335-346. PubMed.
de Meijer, E. P. M., and Hammond, K.M. (2016). The inheritance of chemical phenotype in *Cannabis sativa* L. (V): regulation of the propyl/pentyl cannabinoid ratio, completion of a genetic model. Euphytica 210, 291-307 https://doi.org/10.1007/s10681-016-1721-3. PubMed.
Fawole, I. (2001). Maternal inheritance of plant variegation in cowpea, *Vigna unguiculata* (L) Walp. Theoretical and Applied Genetics 102, 458-462, https://doi.org/10_1007/s001220051667. PubMed.
Frank, M.H., and Chitwood, D.H. (2016). Plant chimeras: the good, the bad, and the 'Bizzaria'. Developmental Biology 119, 41-53; https://doi.org/10.1016/j.ydbio.2016.07.003. PubMed.
Koo, B., Nottenburg, C., and Pardey, P.G. (2004). Plants and Intellectual Property: An International Appraisal. Science 306, 1295-1297; https://doi.org/10.1126/science.1106760. PubMed.
Lata, H., Chandra, S., Techen, N., Khan I.A., and ElSohly, M.A. (2016). In vitro mass propagation of *Cannabis sativa* L.: A protocol refinement using novel aromatic cytokinin meta-topolin and the assessment of eco-physiological, biochemical and genetic fidelity of micropropagated plants. J. of App. Res. on Medicinal and Aromatic Plants 3, 18-26; https://doi.org/10.1016/j.jarmap.2015.12.001. PubMed.
Lata, H., Chandra, S., Khan, I.A., Elsohly, M.A. (2017). Micropropagation of *Cannabis sativa* L.—An Update. In *Cannabis sativa* L.—Botany and Biotechnology.S. Chandra, H. Lata, and M.A. ElSohly, eds. (Oxford, MS: Springer International Publishing), p. 285-297; https://doi.org/10.1007/978-3-319-54564-6_13. PubMed.
Lichtenthaler, H.K. (1987). Chlorophylls and Carotenoids: Pigments of Photosynthetic Biomembranes. Methods in Enzymology 148, 350-382; https://doi.org/10.1016/0076-6879(87)48036-1. PubMed.
Marcotrigiano, M. (1997). Chimeras and variegation: patterns of deceit. HortScience 32, 773-784.
Mohan Jain, S. (2006). Mutation-assisted breeding for improving ornamental plants. Acta Hortic. 714, 85-98 https://doi.org/10.17660/ActaHortic.2006.714.10. PubMed.
Upov Welcome,https://www.upov.int/portal/index.html.en,2021,one page.
Sakamoto, W. (2003). Leaf-variegated mutations and their responsible genes in *Arabidopsis thaliana*. Genes and Genetic Systems 78, 1-9 https://doi.org/10.1266/ggs.78.1. PubMed.
Small, E., and Cronquist, A. (1976). A practical and natural taxonomy for *Cannabis*. Taxon 25, 405-435 https://doi.org/10.2307/1220524. PubMed.
Small, E., and Marcus, D. (2002). Hemp: A new crop with new uses for North America. In Trends in new crops and new uses. J. Janick and A. Whipkey eds (Alexandria, VA: ASHS Press), p. 284-326.
Potter, D. (2009). The propagation, characterisation and optimisation of *Cannabis sativa* L. as a phytopharmaceutical. Thesis for the degree of Doctor of Philosophy (PhD) in Pharmaceutical Sciences, Department of Pharmaceutical Science Research, King's College London, Mar. 2009. 255 pp.
Potter, D. (2013). A review of the cultivation and processing of *cannabis* (*Cannabis sativa* L.) for production of prescription medicines in the UK. Drug testing and analysis. Special Issue: Cannabinoids part II: The current situation with cannabinoids 6, 31-38 https://10.1002/dta.1531. PubMed.

(Continued)

*Primary Examiner* — June Hwu
(74) *Attorney, Agent, or Firm* — Tristan A. Fuierer; Olive Law Group, PLLC

(57) ABSTRACT

The present invention provides a new ornamental variety of *Cannabis sativa* L., named 'Divina'. 'Divina' was developed and obtained from a spontaneous mutation of the parent 'Pilar' and is asexually propagated, having a distinctive "mottled yellow and green leaf" phenotype.

2 Drawing Sheets

(56) References Cited

OTHER PUBLICATIONS

Figure 1A:
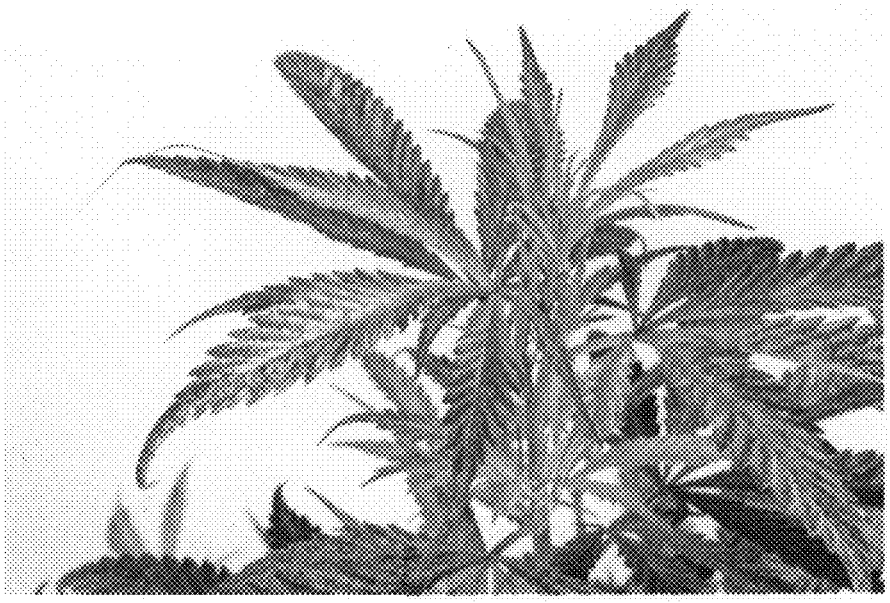

Weiblen G.D., Wenger, J.P., Craft, K.J., ElSohly, M.A., Mehmedic, Z., Treiber, E.L., and Marks, M.D. (2015) Gene duplication and divergence affecting drug content in *Cannabis sativa*. New Phytologist 208, 1241-1250.
Henny R.J and Chen J. 2003. Chapter 6: Cultivar Development of Ornamental Foliage Plants. Plant Breeding Reviews, vol. 23: 245-290.
S. Casano. Development of ornamental *Cannabis sativa* L. varieties. Oral presentation in: 30th International Horticulture Congress, Istanbul (Turkey), Aug. 12-16, 2018. 20 pp.
V. Codesido, M. Marin, C. Sánchez-Camerero Callado, C. Ferreiro-Vera, and S. Casano. Cannabinoids and terpenoids yields of the ornamental *Cannabis sativa* L. variety "Divina" characterized by a variegated foliage as morphological marker. Poster in: 30th International Horticulture Congress, Istanbul (Turkey), Aug. 12-16, 2018. one page.
S. Casano. Avances en investigación, desarrollo, e innovación en materia de mejoramiento vegetal de *Cannabis* medicinal. Oran presentation in: Congreso Nacional de Semillas Acosemillas 2018: Hablemos de biodiversidad e innovación, Bogotá (Colombia), Nov. 8-9, 2018. https://acosemillas.org/wp-content/uploads/2020/08/14.-Phytoplant-Salvatore-Casano.pdf, 41 pp.
CPVO Feb. 2017 Application for community protection Enza, 195 pp.
Proposal for a variety denomination (Divina), Mar. 7, 2017, CPVO, 220 pp.
CPVO 20180057901 Divina, 2018,one page.
Final Report on the technical examination in the framework of Plant Breeders' Rights, Refernce No. HNP77,Enza, 2017, 2pp.
Rasbeschrijving Variety Description HNP77 Enza 2017, 3 pp.
Certificate on the Grant of Community Plant Variety Rights Divine Jul. 16, 2018, 2pp.
CPVO Decision No. 50045 Divina, 2018, one page.
CPVO May 2018, 199 pp.
Variety Data Sheet, https://vf.plantvarieties.eu/varieties/QZ-0-PBR-1282865?lang=en, 2018 one page.

* cited by examiner

*CANNABIS* PLANT NAMED 'DIVINA'

Latin name of the genus and species of the claimed plant: *Cannabis sativa* L.

Variety denomination: 'Divina'.

CROSS REFERENCE TO RELATED APPLICATIONS

Not applicable.

STATEMENT REGARDING FEDERALLY-SPONSORED RESEARCH AND DEVELOPMENT

Not applicable.

FIELD OF THE INVENTION

This invention relates to a new and distinct *Cannabis* ornamental plant with the varietal denomination 'Divina', which is a variety of *Cannabis sativa* L. and a spontaneous mutation of the varietal denomination 'Pilar', one of our registered *C. sativa* varieties which is asexually propagated in our indoor cultivation facilities (Phytoplant Research S.L). 'Divina' is clearly distinguished from the parent plant 'Pilar' by its yellow and green variegated foliage as compared to the solid green foliage of 'Pilar' as well as by other characteristics described below in detail. These are, briefly: lower amount of chlorophyll; slower growth rate and lower final height, producing less total biomass; and lesser yields in cannabidiol (CBD) and Δ9-tetrahidrocannabinol (Δ9-THC) amounts.

BACKGROUND OF THE INVENTION

The differences of opinion between taxonomists supporting monotypic and polytypic concepts on *Cannabis* have not yet been resolved. However, the most accepted opinion is that *Cannabis sativa* L. is a highly variable, hybridized and introgressed, unstructured single plant species (Small and Cronquist, 1976). This wide source of variation present in *Cannabis* genetic resources has permitted breeders to select and develop varieties with specific improved traits to be employed for obtaining medicinal, industrial and food derived products of added value. Breeding and cultivation of new *Cannabis sativa* L. varieties has recently increased due to the worldwide, growing demand in the fields of medicinal, industrial and food businesses. Hundreds of protected varieties are listed in the International Union for the Protection of New Varieties of Plants (UPOV) Plant Variety Database PLUTO, as evidenced when searching for protected varieties of *Cannabis sativa* L. (UPOV code: CANNB_SAT) in the countries that signed the 1991 Act of the UPOV Convention.

The maximum content of the psychotropic compound Δ9-tetrahidrocannabinol (Δ9-THC) on a dry weight basis of the inflorescences in industrial and food varieties is defined at a national level and ranges from 0.2% in European Union, 0.3% in EEUU and up to 1.0% in countries such as Switzerland, Uruguay and Colombia. In the last decade, medicinal varieties with different chemotypes have been selected and a genetic model of inheritance has been completed and proposed by de Meijer and Hammond (2016), resulting in an improved technical knowhow in breeding of medicinal varieties for producing a specific cannabinoid as predominant, or in combination with other cannabinoids.

With the ongoing research and development of industrial and medicinal protected varieties that does not possess contents of Δ9-THC higher than 0.2-1.0%, the possibility of developing ornamental *Cannabis* varieties must be considered, especially when such protected varieties can be easily distinguished from the rest of protected and unprotected varieties through the easy detection of the variegated foliage. Such foliage is a morphological marker that permits an easy and immediate identification of specific protected *Cannabis* varieties commercialized as ornamentals.

Ornamental varieties account more than half of the total applications of plant patents and plant breeder's rights (PBRs) granted in both European Union and United States of America (Koo et al., 2004). Mohar Jain (2006) reported that within more than 2300 mutant varieties officially or commercially released worldwide and registered at Joint FAO/IAEA Mutant Variety Database, 566 represent ornamental varieties. Variegated plants comprise approximately one-third of ornamental plants commercially grown (Gilman, 1996). Behe et al. (1999) reported that consumer preferences for plant characteristics have placed leaf variegation as second most important characteristic to be considered in the purchase decision.

The cause of mutation (and in the case of 'Divina', the resulting leaf variegation) is mostly unknown. It can often appear spontaneously and is called "sporting." Mutation may also be induced by a variety of factors, such as irradiation, chemical application or virus infection. Some methods are extremely accessible and have been employed for centuries, while others involve advanced transgenic techniques listed by Frank and Chitwood (2016). All these factors can change the genome, which in turn may result in the inability to produce properly functional chlorophyll, and thus causing leaf variegation. Leaf variegation in higher plants has long been known as a recessive genetic trait, and it results from a defect that makes chloroplast development unstable, since at least part of the tissues gives rise to normal chloroplasts. Leaf variegation was proposed by Sakamoto (2003) to be a common phenotype of inter-organellar compensation and cytoplasmic sorting processes that minimize the defects in chloroplast and mitochondrial functions.

According to Kirk and Tilney-Basset (1978), variegation can be categorized as either cell lineage or non-cell lineage types. Cell lineage variegation occurs in genetic mosaics (individuals with cells of different genotypes), while in non-cell lineage variegation all cells have the same genotype but the genes responsible for the trait or phenotype are expressed only in some of the cells, e.g., because of differential gene expression (Marcotrigiano, 1997).

Leaf variegations can arise from mutations that make chloroplast formation unstable; while these mutations are most often found in the chloroplast genome they can also occur in the nuclear genome (Sakamoto, 2003). Mutations in the nuclear genome can be distinguished from mutations in the chloroplast genome by the inheritance pattern. More specifically, chloroplast mutations are typically inherited maternally, while mutations in the nuclear genome show Mendelian inheritance (Fawole, 2001).

*Cannabis* genetic resources are highly variable in their aesthetic appearance and in morphological, physiological and biochemical characteristics of relevance. *Cannabis* plants grow quickly and vigorously under optimal growing environments, being generally appreciated as attractive-looking ornamental plant species for the abundant green foliage, the characteristic leaf and the aromatic inflorescences. Because of the legal restrictions on cultivating individual plants, the ornamental industry has never considered this plant species as an ornamental crop. Only the variety 'Panorama' was commercialized as ornamental in Hungary in the 1980s, being bred by Iván Bócsa for its short and strongly-branched growth habit (Small and Marcus, 2002). The limited success of this ornamental variety was mainly caused by the fact that it was not easily distinguishable from the rest of protected, and unprotected *Cannabis* varieties, thereby potentially associating its cultivation as an illegal act.

By contrast, and despite of the potential risk of poisoning for small children and domestic livestock, beautiful and attractive ornamental varieties of toxic, psychotropic or medicinal plant species are widely cultivated in private and public areas, such as for example: pink *oleander* (*Nerium oleander*), yellow *oleander* (*Thevetia peruviana*), *Poinsettia* (*Euphorbia pulcherrima*), *Hydrangea* (*Hydrangea macrophylla*), *Rhododendron* (*Rhododendron ponticum*), Saint Peter cactus (*Echinopsis pachanoi*), wormwood (*Artemisia absinthium*), opium poppy (*Papaver somniferum*), foxglove (*Digitalis purpurea*), periwinkle (*Catharanthus roseus*), etc.

In April 2017, we obtained provisional protection obtained in plant breeder rights (PBR) from the Community Plant Variety Office (CPVO) for the dioecious female ornamental variety 'Divina' (CPVO file number: 2017/0149). During the pendency of the PBR applications, 'Divina' was not publicly available as testing sites for DUS (Distinctness, Uniformity, Stability) trials, such as Naktuinbouw in The Netherlands, are under the control of the CPVO. The PBR application for 'Divina' was originally submitted to the CPVO under the proposed demonination name 'Enza' and subsequently changed to 'Divina'. As of the date of filing of this plant patent application, 'Divina' has not been publicly available or offered for sale anywhere in the world nor has it been offered for sale under another variety name.

'Divina' is one of the first *Cannabis* varieties to obtain protection of plant breeder's rights at the CPVO, granted with decision N° EU 50045 of 16 Jul. 2018. 'Divina' is characterized by a stable variegated foliage of the vegetatively-derived propagated plants. 'Divina' has a distinctive "mottled yellow and green leaf" phenotype as compared to its parent, the medicinal variety 'Pilar' (CPVO Application number 2016/0115; granted with decision N° EU 50009 of 16 Jul. 2018). 'Divina' was detected from a spontaneous bud sport of 'Pilar'. Both 'Divina' and 'Pilar' are characterized by having cannabidiol (CBD) as predominant cannabinoid, instead of Δ9-THC. The distinctness easily detected by using a variegated foliage as morphological marker (FIGS. 1-3) is an impetus in the commercialization of ornamental *Cannabis* varieties such as 'Divina'.

We were interested in performing a direct comparison between DNA fingerprinting of the mutated variety 'Divina' and the parent variety 'Pilar'. We used a set of 15 Simple Sequence Repeat (SSR) markers used for ensuring genetic authenticity and traceability, and for enforcing PBRs of protected varieties at our company. Besides the interest in detecting differences at genotypical and phenotypical levels, we were also interested in detecting potential differences at microscopic and chemotypical levels. For this reason, a molecular marker for Δ9-THCA and CBDA synthases, gas chromatography, conventional and advanced microscopy were used as tools to research on the distinct morphological and physiological characteristics of genetically distinct cells, the "green cell" and the "yellow cell". An objective of this study was to detect differences and to evaluate the correlations between the mutated variety 'Divina' and the unmutated parent variety 'Pilar'.

Plants of the variety 'Divina' have a significant lower content of chlorophyll in their leaves than plants of the variety 'Pilar'. A slower growth rate and less total biomass production have been generally observed when mother plants of both varieties are grown at similar conditions under long daylength, supposedly due to the inability of 'Divina' to synthesize chlorophyll in portions of the photosynthetic organs. The main objectives of the second example described below were to evaluate yield losses or gains in vegetal raw material components (stalks, leaves and inflorescences) between the mutated variety 'Divina' and the parent variety 'Pilar', as well as cannabinoid and terpenoid yields. A comparative production trial between plants of the mutated variety 'Divina' and plants of the un-mutated variety 'Pilar' was set in the same trial location for evaluating yield losses or gains in vegetal raw material components (stalks, leaves and inflorescences). Cannabinoid and terpenoid yields and possible changes in specific secondary metabolites due to genomic mutation were also examined. Our studies showed differences in CBD and Δ9-THC amounts in 'Pilar' vs. 'Divina'.

BRIEF SUMMARY OF THE INVENTION

The present invention provides a new and distinct ornamental variety of *Cannabis sativa* L. with a varietal denomination of 'Divina'. Briefly, 'Divina' was identified as a spontaneous mutation of the varietal denomination 'Pilar'. The variety 'Divina' has a distinctive "mottled yellow and green leaf" phenotype as compared to the green-leafed parent variety 'Pilar'. 'Divina' also differs from the parent plant 'Pilar' in having a lower amount of chlorophyll (about 73% of 'Pilar'), slower growth and lower height, less biomass, and lower CBD content (less than 4%) and lower Δ9-THC content (less than 0.4%) in inflorescences than 'Pilar'. Further details are provided below.

'Divina' obtained a certificate of plant breeder's rights at the CPVO, granted with decision N° EU 50045 of 16 Jul. 2018. The origin of this new variety is one individual clone of 'Pilar' cultivated in a high technology greenhouse, placed within the Rabanales Campus of the University of Còrdoba (Spain), for trialing 4 different fertilizer regimes on a clonal population of 240 individuals (60 individuals per 4 treatments) of the variety 'Pilar', in which a spontaneous variegated plant part was detected in the apical bud some days after transferring the clones in the greenhouse, on 25th of May 2015. The individual plant was placed in the border area of one of the four cultivation tables used for the trial, making it more easy to visually identify the bud sport mutation in the apical part of the individual plant. Constant environmental conditions were ensured to all the 240 plants placed within the cultivation area, including the border areas, wherein the only difference is the application of 4 different fertilizer regimes. The first asexual propagation of the chimera started the 17th of June 2015 by taking only 1 cutting, which successfully rooted after approximately 2 weeks. This individual clone was then cultivated and cloned and subjected to further cycles of selective cloning to fix this distictive attribute in our indoor facilities. A selected mother plant of the seventh generation of the chimera with all the leaves variegated was selected and cloned on 11th of January 2017, 6 weeks later from transplanting several cuttings rooted of the seventh generation of the chimera. This process resulted finally in fully variegated plants of a new variety, presented here as 'Divina'.

The mutated plant 'Divina' was detected and isolated from a bud sport of the donor plant ('Pilar') asexually propagated in our indoor cultivation facilities (Phytoplant Research S.L.) placed in an industrial warehouse in Cordoba (Spain). The indoor cultivation facilities of the company are authorized as an official nursery by the Junta of Andalucia Phytosanitary Office (ROPCIV code 14-0449, according to UE 2016/2031, art. 65.1). The first stable variegated clone, used as the mother plant for future generations, was obtained after seven generations of asexual propagation of the original isolated chimera. Approximately 12-13 generations have been tested for stability. Asexual propagation is commonly performed by in vivo rooted cuttings of medicinal varieties (Potter, 2013), but also effective in vitro shoot micropropagation protocols have been developed (Lata et al., 2017). Elite stock plants are maintained in repositories in vegetative stage under artificially created long daylength controlled environment for generating propagules for in vivo or in vitro propagation. A protocol for all the stages of in vitro micropropagation is already established at our laboratories. Propagation of true-to-type variegated 'Divina' rooted cuttings can be performed satisfactorily by adopting good in vivo and in vitro propagation practices and the clones are identical to the original 'Divina' in all distinguishing characteristics. Cuttings from 'Divina' have demonstrated that the combination of characteristics disclosed herein are stable and firmly fixed, and are retained true-to-type.

When considering the sexual propagation of the variety, all the F1-hybrid offspring obtained by crossing a dioecious "green leaf" male plant with a 'Divina' plant show a "green leaf" phenotype.

Both 'Divina' and 'Pilar' varieties show the same genotype when DNA fingerprinting is performed by using 15 SSR molecular markers. Additionally, by using a molecular marker for Δ9-THCA/CBDA synthases it was confirmed that only the alleles for CBDA synthase can be detected in both varieties, as it is also confirmed by using gas chromatography that both varieties have a CBD chemotype.

The content of the psychotropic compound Δ9-THC in inflorescences of 'Divina' plants was lower than 0.4% in all the samples analyzed at our laboratories. The content of CBD was less than 4% in inflorescences of 'Divina' plants (Codesido et al., 2018). Microscope observations of "yellow" portions of stalks, leaves and inflorescence bracts confirm the presence of bulbous, sessile- and capitate-stalked trichomes.

'Divina' cuttings are more prone to fungal disease during in vivo rooting stage than 'Pilar' cuttings, however satisfactory percentages of true to type rooted cuttings can be achieved by adopting good propagation practices. In artificial growing conditions the variety 'Pilar' achieved significantly higher cannabinoids and terpenoids yields than the variety 'Divina'. Slight differences of terpenoid composition were also detected.

Plants of the present invention have not been observed under all possible environmental and cultural conditions. The phenotype may vary somewhat with variations in environmental conditions, especially when plants are exposed to completely natural conditions, without, however any variance in the genotype. For example, phenotypic expression may vary somewhat with fluctuations in temperature and CO2, light spectra and intensity, substrate volume and chemistry, for mentioning the most influential parameters.

BRIEF DESCRIPTION OF THE PHOTOGRAPHS

The accompanying colored photographs illustrate the overall appearance of 'Divina' showing the colors as true as it is reasonably possible to obtain in colored reproductions of conventional photography. The photographs were taken in a greenhouse setting under defused, natural lighting.

Figure 1B:
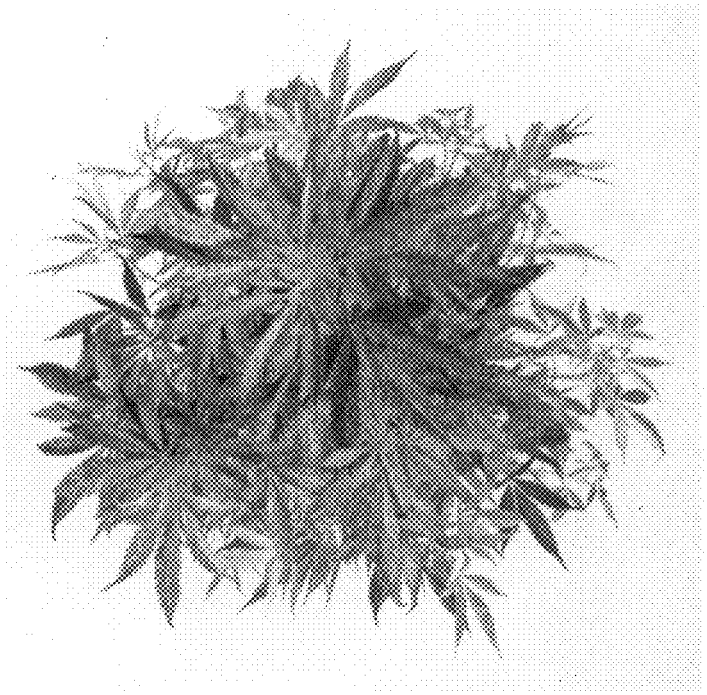

FIG. 1A-B: FIGS. 1A and 1B show a close up view of the yellow and green variegated foliage of the 'Divina' variety and top view of the plant, respectively. The photograph is of a stock plant of approximately six weeks of age maintained under 18 hours/day of artificial lighting (400-600 μmol $m^{-2}s^{-1}$), under controlled temperatures and relative humidity, and CO2 enriched up to 800 ppm.

Figure 2:
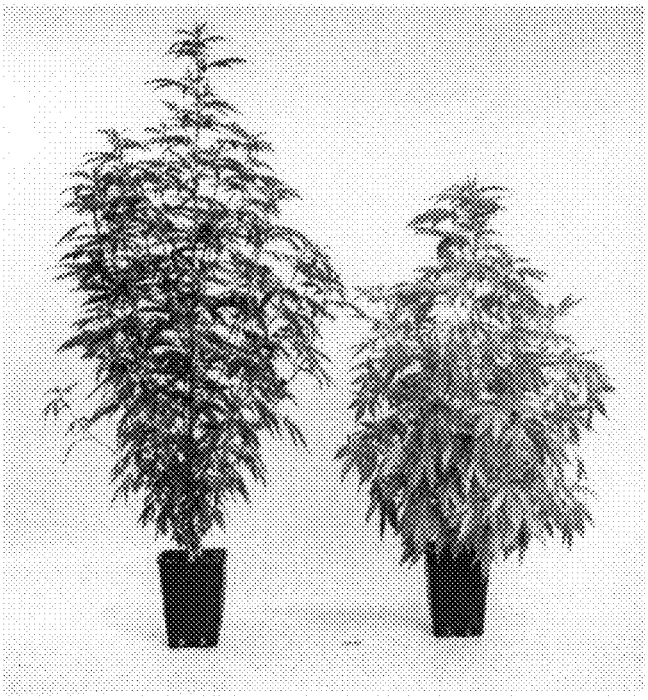

FIG. 2: FIG. 2 shows individual plants of the 'Pilar' (left) and 'Divina' (right) varieties for purposes of comparison of leaf color, variegation, and size. The parent plant 'Pilar' has green foliage while the spontaneous mutant 'Divina' has variegated yellow and green leaves. Under the same growth conditions, 'Divina' is shorter than 'Pilar'. The photograph is of stock plants of approximately six weeks of age maintained under 18 hours/day of artificial lighting (400-600 μmol $m^{-2}s^{-1}$), under controlled temperatures and relative humidity, and CO2 enriched up to 800 ppm.

Figure 3:
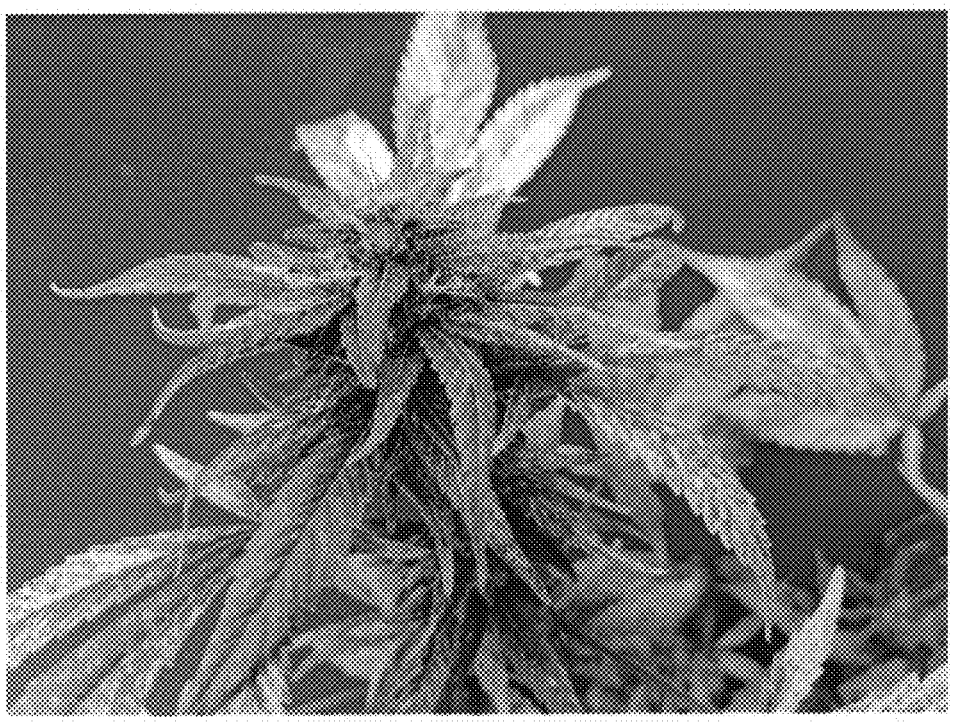

FIG. 3: FIG. 3 shows a close up view of a 'Divina' flower and attached leaves of an auxillary branch. The photograph is of a flowering plant of ten weeks of age; four weeks of vegetative stage and six weeks of reproductive stage.

EXAMPLES

Example 1

Development of an Ornamental *Cannabis sativa* L. Variety: Phytochemical, Morphological, Genetic Characterization and Propagation Aspects

MATERIALS AND METHODS

The spontaneously mutated type chimera was detected on $25^{th}$ of May 2015 and isolated from a mutated donor plant growing in greenhouse. Only one cutting was isolated and rooted from the first generation of the chimera and, after various generations of vegetative propagation of selected cuttings developing a partially variegated leaf foliage in derived mother plants, leaf variegation in all the leaves of selected mother plants was achieved starting from the seventh generation of the chimera. Some other not selected mother plants at this generation were still expressing some individual "not mottled green leaf" and/or "not mottled yellow leaf", and even "not mottled green branch" and/or "not mottled yellow branch." Other chimeras have been detected in different mother plants of the variety 'Pilar', suggesting its high propensity to develop spontaneous mutations.

DNA of three leaf samples taken from elite stock plants maintained in the repository were extracted by using the DNeasy Plant Mini Kit (Cat No./ID: 69104) from Qiagen. DNA samples were identified as: "Pilar not mottled green leaf", "Divina variegated leaf", and "Divina not mottled yellow leaf" and sent to the Center for Research in Agricultural Genomics (CRAG), which is a public consortium formed by various Spanish institutions (CSIC, IRTA, UAB and UB) and placed in Barcelona. The set of 15 SSRs and the molecular marker for Δ9-THCA/CBDA synthases were developed and carried out by researchers at CRAG. After confirming the good quality of the received DNA samples, PCR amplification of 15 SSR markers labelled with fluorescence was performed, followed by separation and detection of SSRs using an automatic sequencer of type ABI Prism® 3130xl (Applied Biosystems). Genetic analysis was performed with software GeneMapper® Version 4.0 (Applied Biosystems). The molecular marker for Δ9-THCA/

CBDA synthases and 15 molecular markers are not publicly disclosed, being these identified with increasing numbers from CAN1 to CAN15.

Two different microscopic techniques were employed for detecting extracellular and intracellular variability between leaf samples (in the form of discs with 1 cm of diameter) identified as "Pilar not mottled green leaf" and "Divina not mottled yellow leaf". A conventional microscopy approach by using the binocular microscope BA310 from Motic was employed to visually detect and confirm the presence of glandular trichomes in the upper and lower surface of leaf discs, as well as in "yellow stalks" and "yellow inflorescences bracts". An advanced microscopy approach by using a transmission electron microscopy JEOL JEM-1400 (TEM) from SEMTech Solutions was employed to study the differences in cell organelles of leaf discs and to take images. Leaf discs for TEM visualization were stored in glutaraldehyde solution until were sent to the Servicio Central de Apoyo a la Investigación (SCAI) of the University of Córdoba, where researchers prepared samples by dehydrating, fixing and cutting them into very thin cross-sections by using the ultramicrotome ULTRACUT R from Leica for preparing microscope grids. TEM images of cell organelles were obtained and analyzed in collaboration with a specialist in Anatomy and Pathological Anatomy Compared.

A comparative rooting trial was performed by taking 180 cuttings from elite stock plants of each variety maintained in the repository at Phytoplant Research S.L. The basal part of the cutting was immersed in a liquid rooting product (Inabar) containing natural phytohormones, and then treated cuttings were placed in Jiffy cubes (model 7; 44 mm) disposed in propagation greenhouses where 60 treated cuttings can be placed in each unit during the in vivo rooting stage. The range adopted for climatic parameters were: 22±1° C., 75-85% of relative humidity, 350-400 ppm of carbon dioxide, and under a photon flux density of approximately 100 μE mol $m^{-2}s^{-1}$ provided by light-emitting diodes (LEDs) lights under continuous daylength (24 hours light/day). After three weeks from taking cuttings, data were taken for dead cuttings from fungal disease and for healthy rooted cuttings.

At the same time, a generic protocol for all the stages of in vitro micropropagation already established at Phytoplant Research S.L. laboratories for axillary shoots of the variety 'Pilar' was also tested for performing the in vitro micropropagation shoots of the variety 'Divina'. Shoots were incubated in a growth chamber (model A1000 from Conviron) and the range adopted for climatic parameters were: 25±1° C., 70-80% of relative humidity, 350-400 ppm of carbon dioxide, and under photon flux density of approximately 225 μE mol $m^{-2}s^{-1}$ provided by fluorescent tubes under long daylength (18 hours light/day). A batch of F1-hybrid seeds was produced by using a dioecious "green leaf" male selected plant ("79/4/1/5/1") as a male parental plant. 73 F1-hybrid seeds of the cross "79/4/1/5/1" X 'Divina' were germinated and cultivated during a period of 14 weeks under artificially created long daylength controlled environment for evaluating the expression of variegated leaves in plants of the F1-hybrid offspring.

RESULTS AND DISCUSSION

By using the molecular marker system developed at CRAG we have been previously able to distinguish several *Cannabis* genetic resources included in CRAG database, ranging from unprotected to protected varieties, both sexually propagated monoecious and dioecious varieties as well as asexually propagated dioecious female varieties (data not shown). In Tables 1, 2, 3 are shown the alleles detected (in base pairs) with the 15 SSR markers. Both varieties 'Divina' (identified as "Divina variegated leaf") and 'Pilar' (identified as "Pilar not mottled green leaf") shown the same genotype when DNA fingerprinting was performed by using 15 SSR markers, as well as when analyzing a mutant "yellow leaf" phenotype sample (identified as "Divina not mottled yellow leaf"). The lack of genetic differences in base pairs of the alleles detected, especially between samples of "Pilar not mottled green leaf" and "Divina not mottled yellow leaf", evidenced that the spontaneous genetic mutation resulting in plant tissues devoid of chlorophyll cannot be detected by the 15 SSR markers. The SSRs CAN2, CAN5, CAN7, CAN12a and CAN14 were homozygous in the three samples 'Divina', "Divina not mottled yellow leaf" and 'Pilar' (see Tables 1, 2, 3).

Tables 1-3. Alleles detected (in base pairs) with molecular markers identified from CAN1 to CAN5 (Table 1), from CAN6 to CAN10 (Table 2), from CAN11 to CAN15 (Table 3). The abbreviation "Divina yellow" is used for samples of "Divina not mottled yellow leaf".

TABLE 1

| SAMPLE ID | CAN1 | | CAN2 | | CAN3 | | CAN4 | | CAN5 | |
|---|---|---|---|---|---|---|---|---|---|---|
| 'Divina' | 121 | 130 | 162 | 162 | 213 | 225 | 282 | 287 | 115 | 115 |
| "Divina yellow" | 121 | 130 | 162 | 162 | 213 | 225 | 282 | 287 | 115 | 115 |
| 'Pilar' | 121 | 130 | 162 | 162 | 213 | 225 | 282 | 287 | 115 | 115 |

TABLE 2

| SAMPLE ID | CAN6 | | CAN7 | | CAN8 | | CAN9 | | CAN10 | |
|---|---|---|---|---|---|---|---|---|---|---|
| 'Divina' | 165 | 167 | 214 | 214 | 267 | 269 | 158 | 175 | 185 | 188 |
| "Divina yellow" | 165 | 167 | 214 | 214 | 267 | 269 | 158 | 175 | 185 | 188 |
| 'Pilar' | 165 | 167 | 214 | 214 | 267 | 269 | 158 | 175 | 185 | 188 |

TABLE 3

| SAMPLE ID | CAN11 | | CAN12a | | CAN13 | | CAN14 | | CAN15 | |
|---|---|---|---|---|---|---|---|---|---|---|
| 'Divina' | 208 | 223 | 287 | 287 | 280 | 288 | 260 | 260 | 160 | 164 |
| "Divina yellow" | 208 | 223 | 287 | 287 | 280 | 288 | 260 | 260 | 160 | 164 |
| 'Pilar' | 208 | 223 | 287 | 287 | 280 | 288 | 260 | 260 | 160 | 164 |

Additionally, by using a molecular marker for Δ9-THCA/CBDA synthases it was confirmed that only the alleles for CBDA synthase can be detected in both varieties, as it was confirmed by using gas chromatography that both varieties have a CBD rich-chemotype. In fact, in Table 4 are shown the alleles detected at the B locus, known for determining *Cannabis* chemical phenotype. A model involving one locus, B, with two alleles, B(D) and B(T), have been proposed (de Meijer et al., 2003), with the two alleles being codominant. However, recently Weiblen et al. (2015) suggested that Δ9-THCA and CBDA synthases are possibly encoded by more than one locus and that these loci are genetically linked. Pure CBD chemotype plants are supposedly due to homozygosity at the B locus and only the alleles B(D)/B(D) were detected and expressed as CBDA synthase. The content of Δ9-THC in inflorescences of 'Divina' plants was lower than 0.4% in all the samples analyzed at our laboratories by gas chromatography, while CBD content was lower than 4% (Codesido et al., 2020).

TABLE 4

Alleles detected [B(D)or B(T)] at B locus with a molecular marker for Δ9-THCA/CBDA synthases.

| SAMPLE ID | Δ9-THCA/CBDA synthases | |
|---|---|---|
| "Divina variegated leaf" | B(D) | B(D) |
| "Divina not mottled yellow leaf" | B(D) | B(D) |
| "Pilar not mottled green leaf" | B(D) | B(D) |

Binocular microscope observations of "yellow" portions of stalks, leaves and inflorescence bracts of 'Divina' variety confirmed the presence of bulbous, sessile- and capitate-stalked trichomes in "yellow" portions of stalks and inflorescence bracts, as well as in both upper and lower surface of leaf discs, with a higher concentration of glandular trichomes in the upper surface. In some samples of leaf discs of 'Divina', especially in the "yellow" portions of upper surface of leaf discs, we have observed anthocyanins accumulation. In other observations on plants of 'Divina' and 'Pilar' cultivated under different artificially created long daylength controlled environments, we have detected that under certain undisclosed conditions the accumulation of anthocyanins can be visually observed in 'Divina' apical leaves directly exposed to artificial light, while cannot be observed in 'Pilar'.

Transmission electron microscopy observations on leaf discs permitted us to detect evident differences in cell organelles from the two genetically distinct cells, "green cell" and "yellow cell". In "yellow cell" highly vacuolated leucoplasts were detected; however, nuclei exhibit usual shape as in "green cell", meaning that they are normally performing the function of governing gene expression and facilitating DNA replication during the cell cycle. Leucoplasts are involved in monoterpene biosynthesis and several secretory cells contain true leucoplasts, devoid of thylakoids and ribosomes (Cheniclet and Carde, 1985). However, in leucoplasts of "yellow cell" thylakoids were detected as well as granules. Those granules were also identified in "green cell" and could be tentatively considered as terpenic granules, which supposedly discharge their content to the vacuole; however, it is still not known how occur the mechanism of transportation of terpenes from one region to another region within the plant cell or to outside the plant body.

The results of the comparative rooting trial have shown significant differences at the 0.05 level when one-population t-Tests were performed on obtained data, except for the % of not rooted cuttings. 'Divina' cuttings were significantly (p=001874) more prone (21.7%) to fungal disease during in vivo rooting stage than 'Pilar' cuttings (3.3%), being particularly susceptible those cuttings having a less lignified stalk. A significantly (p=0.00844) higher % of healthy rooted cuttings was achieved with 'Pilar' cuttings (92.2%), however satisfactory percentages can be also achieved with 'Divina' cuttings (70.6%). A protocol for all the stages of in vitro micropropagation was already established at our laboratories, and it was the same protocol generally adopted for shoot tips of the variety 'Pilar'. After the surface-sterilization of axillary shoot tips, they were introduced in vitro where they generally lasted nine weeks, and then additional two weeks for ex vitro hardening before being used as propagation material.

Three steps were performed in vitro by using the same medium composition but by changing volume and type of containers: 1. induction of shoots (1 mL in multi-well plates for 1 week), elongation of shoots (5 mL in de Wit tubes for 4 weeks), and rooting (50 mL in Eco2Box oval containers for 4 weeks). The medium used was: Formula β (Casano and Grassi, 2009)+3% (w/v) sucrose at the step 1 and 1.5% (w/v) sucrose during steps 2 and 3+0.8% (w/v) agar+2.0 μM meta-Topolin (Lata et al., 2016), at pH=5.8.

When considering the sexual propagation of the variety, all the F1-hybrid offspring composed of 73 plants obtained by crossing a dioecious "green leaf" male plant with a 'Divina' plant shown a "green leaf" phenotype, confirming that leaf variegation is a recessive genetic trait, and that voluntary or involuntary pollination of 'Divina' female inflorescences should not be used for the transmission of the trait leaf variegation in directly derived F1-hybrid offspring.

CONCLUSIONS

Although no differences were detected at genotypical level between 'Divina' and 'Pilar' varieties by adopting specific molecular markers, evident differences can be detected at phenotypical level, especially when "green cell" and "yellow cell" are examined more in details. Next generation sequencing technologies need to be applied in both varieties for discovering exactly where the mutation occurs, if in the nuclear or chloroplast genome. Further cytological, chemical, genetic, and molecular research need to be performed to study the biological nature of the mutated type chimeras, and to unveil the genetic inheritance and sexual transmission of the trait leaf variegation to other *Cannabis* genetic resources. Propagation of true to type variegated 'Divina' rooted cuttings can be performed satisfactorily by adopting good in vivo and in vitro propagation practices.

Literature Cited

Behe, B., Nelson, R., Barton, S., Hall, C., Safley, C. D., and Turner, S. (1999). Consumer Preferences for *Geranium* Flower Color, Leaf Variegation, and Price. HortScience 34, 740-742.

Casano, S., and Grassi, G. (2009). Valutazione di terreni di coltura per la propagazione in vitrodella canapa (*Cannabis sativa* L.). Italus Hortus 16, 109-112.

Casano, S. (2019). Development of ornamental *Cannabis sativa* L. cultivars: phytochemical, morphological, genetic characterization and propagation aspects. Acta Horticulturae, 1263, 283-290 https://doi.org/10.17660/ActaHortic.2019.1263.37.

Cheniclet, C., and Carde, J. P. (1985). Presence of leucoplasts in secretory cells and of monoterpenes in the essential oil: a correlative study. Journal of Botany 34, 219-238.

Codesido, V., Marín, M., Sánchez-Carnerero Callado, C., Ferreiro-Vera, C., and Casano, S. (2020). Cannabinoids and terpenoids yields of the ornamental *Cannabis sativa* L. cultivar 'Divina' characterized by a variegated foliage as morphological marker. Acta Horticulturae, 1287, 161-168 https://doi.org/10.17660/ActaHortic.2020.1287.21.

de Meijer, E. P. M., Bagatta, M., Carboni, A., Crucitti, P., Moliterni, V. M., Ranalli, P., and Mandolino, G. (2003). The inheritance of chemical phenotype in *Cannabis sativa* L. Genetics 163, 335-346. PubMed de Meijer, E. P. M., and Hammond, K. M. (2016). The inheritance of chemical phenotype in *Cannabis sativa* L. (V): regulation of the propyl/pentyl cannabinoid ratio, completion of a genetic model. Euphytica 210, 291-307 https://doi.org/10.1007/s10681-016-1721-3. PubMed Fawole, I. (2001). Maternal inheritance of plant variegation in cowpea, *Vigna unguiculata* (L.) Walp. Theoretical and Applied Genetics 102, 458-462 https://doi.org/10.1007/s001220051667. PubMed Frank, M. H., and Chitwood, D. H. (2016). Plant chimeras: The good, the bad, and the 'Bizzaria'. Developmental Biology 419, 41-53 https://doi.org/10.1016/j.ydbio.2016.07.003. PubMed Gilman, E. F. (1996). Betrock's Florida Plant Guide. Betrock Information Systems, Hollywood, Fla.

Kirk, J. T. O., and Tilney-Bassett, R. A. E. (1978). The plastids: Their chemistry, structure, growth and inheritance, 2$^{nd}$ eds (Amsterdam, N.Y. and Oxford: Elsevier/North-Holland Biomedical Press), pp.960.

Koo, B., Nottenburg, C., and Pardey, P. G. (2004). Plants and Intellectual Property: An International Appraisal. Science 306, 1295-1297 https://doi.org/10.1126/science.1106760. PubMed Lata, H., Chandra, S., Techen, N., Khan I. A., and ElSohly, M. A. (2016). In vitro mass propagation of *Cannabis sativa* L.: A protocol refinement using novel aromatic cytokinin meta-topolin and the assessment of eco-physiological, biochemical and genetic fidelity of micropropagated plants. J. of App. Res. on Medicinal and Aromatic Plants 3, 18-26 https://doi.org/10.1016/j.jarmap.2015.12.001. PubMed Marcotrigiano, M. (1997). Chimeras and variegation: patterns of deceit. HortScience 32, 773-784.

Mohan Jain, S. (2006). Mutation-assisted breeding for improving ornamental plants. Acta Hortic. 714, 85-98 https://doi.org/10.17660/ActaHortic.2006.714.10. PubMed PLUTO (UPOV Plant Variety Database). (2018). http://www.upov.int/pluto.

Sakamoto, W. (2003). Leaf-variegated mutations and their responsible genes in *Arabidopsis thaliana*. Genes and Genetic Systems 78, 1-9 https://doi.org/10.1266/ggs.78.1. PubMed Small, E., and Marcus, D. (2002). Hemp: A new crop with new uses for North America. In Trends in new crops and new uses. J. Janick and A. Whipkey eds (Alexandria, Va.: ASHS Press), p.284-326.

Weiblen G. D., Wenger, J. P., Craft, K. J., ElSohly, M. A., Mehmedic, Z., Treiber, E. L., and Marks, M. D. (2015) Gene duplication and divergence affecting drug content in *Cannabis sativa*. New Phytologist 208, 1241-1250

Example 2

Cannabinoid and Terpenoid Yields of the Ornamental *Cannabis sativa* L. Variety 'Divina' Characterized by a Variegated Foliage as Morphological Marker

MATERIALS AND METHODS

The method described by Lichtenthaler (1987) for extracting and quantifying chlorophyll in μg/mL was employed to measure chlorophyll in 'Pilar' (not mottled green leaves) and in 'Divina' (variegated leaves) from 6 samples of each variety taken from representative leaves directly exposed to artificial light. Sampled mother plants were cultivated under long daylength and used as sources of propagules for the in vivo rooted cuttings used in the trial.

The comparative production trial was performed at Phytoplant Research authorized facilities in Córdoba (Spain). A cabinet for indoor cultivation of 2 $m^2$ of cultivated area. A total of eight plants for each variety (8 plants/$m^2$) were cultivated. The cabinet was equipped with two 600 W/$m^2$ Philips Greenpower 600W 400V EL lights providing a photon flux density of approximately 700 μmol $m^{-2}s^{-1}$. Plants were cultivated in 8.5 L pots filled and maintained for 4 weeks in vegetative stage under long daylength (18 hours light/day) and then induced to flower under short daylength (12 hours light/day) and maintained for additional 5 weeks, when plants were harvested and data on individual plant height and total fresh weight (FW) were taken. The range adopted for climatic parameters were: 25±3° C., 50-70% of relative humidity, and 350-400 ppm of carbon dioxide. Plants were cultivated on a coconut natural growth medium (Coco Professional Plus, Canna Continental, Los Angeles, Calif.) and nutrient solutions were prepared by using the fertilizers Coco A+B from Canna Continental. Nutrient solution was applied to plants at variable values of electrical conductivity during the various phenological stages (from 1.2 to 1.8 mS/cm; 0.4 mS/cm during the last week of cultivation).

After the drying stage, data on total dry weight (TDW) were obtained after manual processing, separation and taking the respective data on dry weights of vegetal raw material components: leaves (LDW), inflorescences (FDW), and stalks (SDW). Approximately five grams of inflorescences and five grams of leaves were sampled for each one of the 16 plants. Samples were differently prepared, stored and extracted before cannabinoids and terpenoids analysis, depending from the secondary metabolites to be analyzed.

For cannabinoid analysis an Agilent 7890 B gas chromatograph was used. Separation of compounds was performed by using a fused silica capillary column Rxi-35Sil MS (15 m×0.25 mm I.D., 0.25 μm thickness of the film). Gas carrier was helium (99.9%) with a flow of 2.5 mL/min. The program of the oven was as follows: 200° C. as starting temperature, maintained during 0.1 min, increasing 120° C./min up to 250° C. maintained during 5 min and 50° C./min up to 300° C. Injection of 1 μL at 250° C. in Splitless. Compounds were detected by mass spectrometry using a MS 5977B from Agilent. The transfer line was maintained at 330° C., the source of ionization at 230° C. and the quadrupole at 150° C. Data acquisition was by SCAN mode, with an interval of m/z between 40 and 400.

For terpenoid analysis, an Agilent 7820 B gas chromatograph was used. Separation of compounds was performed by using a fused silica capillary column HP-5MS UI (30 m×0.25 mm I.D., 0.25 μm thickness of the film). Gas carrier was helium (99.9%) with a flow of 1.5 mL/min. The program of the oven was as follows: 50° C. as starting temperature, maintained during 0.1 min, increasing 4° C./min up to 70° C. maintained during 14 min, 6° C./min up to 77° C. maintained during 9.5 min, 50° C./min up to 165° C., 1° C./min up to 170° C. and 25° C./min up to 300° C., maintained during 5 min. Injection at 220° C. in splitless of 1 μL. The detector was maintained at 300° C. by employing 35 mL/min of H2, 350 mL/min of air and 25 mL/min of $N_2$, registering the signal of instrument at 20 Hz.

The data were subjected to t-Student Test to evaluate the significance of differences on means of the different media by using MicroCal Origin version 4.1 statistical software package.

RESULTS AND DISCUSSION

Results obtained on chlorophyll contents by using the destructive method described by Lichtenthaler (1987) have confirmed that plants of the variety 'Divina' had a significant lower content of chlorophyll than plants of the variety 'Pilar', being 10.97 μg/mL the average chlorophyll content of the leaves of the variety 'Divina', representing 73% of the average detected in leaves of the variety 'Pilar', which was 15.02 μg/mL (Table 5). These results confirmed the observations that plants of the variety 'Divina' had generally a slower growth rate and less total biomass production when mother plants of both varieties were grown at similar conditions under long daylength, supposedly due to the inability to synthesize chlorophyll in portions of the photosynthetic organs (Codesido et al., 2020).

TABLE 5

Chlorophyll contents in different samples of 'Divina' and 'Pilar' varieties.

| SAMPLE ID | Clorophyll content (μg/mL) | SD | SE | Sum | N |
|---|---|---|---|---|---|
| 'Divina' | 10.97 | 1.51 | 0.61 | 65.79 | 6 |
| 'Pilar' | 15.02** | 2.97 | 1.21 | 90.12 | 6 |

**mean significant statistical differences by using the t-student test; $p < 0.05$ Significant differences at the 0.05 level were shown when one-population t-Student Test was performed on some of the obtained data. Data confirmed previous observations on mother plants of both varieties grown at similar conditions under long daylength, and shown that in artificial growing conditions flowered plants of the variety 'Pilar' achieved a significantly higher height ($p=9.36E^{-5}$) and SDW ($p=0.046$) than flowered plants of the variety 'Divina', confirming that a deprived photosynthetic activity result in less total biomass accumulation in the stalks, the only vegetal raw material component not of interest for obtaining *Cannabis*-based medicines. In fact, no significant differences were found on FW, TDW, LDW and FDW, confirming that similar yield of the vegetal raw material components (leaves and inflorescences) used for extracting cannabinoids and terpenoids can be obtained from both varieties, although slightly higher yields on LDW and FDW were obtained from plants of the variety 'Pilar'.

Significant differences at the 0.05 level were shown when one-population t-Student tests were performed on most of the obtained gas chromatographic data on CBD, Δ9-THC, and total terpenoids contents in leaves and inflorescences. Concentrations of most analytes were significantly higher in samples of 'Pilar' variety. No significant differences were found on Δ9-THC content in leaves ($p=0.05$) and total terpenoids content in inflorescences ($p=0.69$). Average contents of CBD were significantly lower in inflorescences (3.22%) and in leaves (1.57%) in plants of the variety 'Divina' (respectively $p=2.16E^{-6}$ and $p=0.00883$). In a similar way, average contents of the psychotropic compound Δ9-THC were significantly lower in inflorescences (0.34%) and in leaves (0.15%) in plants of the variety 'Divina' confirming that the potential risk of abuse is inferior than with plants of the variety 'Pilar'. Average contents of total terpenoids in plants of the variety 'Divina' were 0.80% in inflorescences and 0.34% in leaves, with average contents of total terpenoids in inflorescences not being significantly different between plants of the different varieties.

The results obtained on cannabinoid contents of 'Divina' variety are not completely in agreement with the results from a previous study (Potter, 2009) performed on an unprotected *Cannabis* variety with variegated portions of foliage. In fact, Potter (2009) reported that leaf tissues lacking chlorophyll suffered no reduction in cannabinoid synthesis and accumulation abilities, as a small but significantly higher concentration of cannabinoids (weight per unit area) was found in tissues lacking in chlorophyll, demonstrating that plant tissues devoid of chlorophyll could support the synthesis and accumulation of cannabinoids within their own glandular trichomes, and that the carbon source required would have been produced elsewhere within the plant and then translocated to these glandular trichomes, where synthesis and accumulation of cannabinoids takes place.

Our results suggest that synthesis and accumulation of cannabinoids in glandular trichomes within inflorescences and leaves tissues devoid of chlorophyll may be inferior than in tissues with higher content of chlorophyll. We detected an opposite behavior on terpenoid content in inflorescences, suggesting that glandular trichomes within inflorescence tissues devoid of chlorophyll have a similar terpenoid synthesis and accumulation to glandular trichomes within inflorescence tissues with higher content of chlorophyll. At the same time, the detected terpenoid content in leaves does not support the results obtained in inflorescences, but the different ratios of sessile and capitate stalked glandular trichomes present in leaves and inflorescence tissues may explain the results obtained in this study.

Results were obtained showing that in artificial growing conditions the variety 'Pilar' achieved significantly higher average cannabinoid and terpenoid yields than the variety 'Divina'. In fact, plants of the variety 'Pilar' achieved a significant ($p=0.017$) higher average CBD yield per plant (1.79 g of CBD/plant) than the average CBD yield per plant of the variety 'Divina' (1.29 g of CBD/plant), as well as a significant ($p=0.00026$) higher average Δ9-THC yield per plant (0.18 g of Δ9-THC/plant) than the average Δ9-THC yield per plant of the variety 'Divina' (0.13 g of Δ9-THC/plant). In addition, a significant ($p=0.0042$) higher average in the yield of total terpenoids per plant (0.40 g of total terpenoids/plant) was obtained for 'Pilar' than for the variety 'Divina' (0.30 g of total terpenoids/plant). Interestingly, the yields obtained on these secondary metabolites by the leaf component were always higher than the yields obtained from the inflorescences, confirming that both components are of interest for extracting cannabinoids and terpenoids. Also, the average CBD yield obtained per plant of the variety 'Divina' (1.29 g of CBD/plant) represents 72% of the average CBD yield obtained per plant of the variety 'Pilar' (1.79 g of CBD/plant). This primary productive parameter seems to be directly correlated with the ratio of chlorophyll contents between 'Divina' and 'Pilar' varieties, which was 73%.

By comparing contents of main terpenoids (expressed as % on w/w basis) determined in inflorescences and leaves of both varieties, slight differences in terpenoid composition were detected. In fact, while slightly higher contents in all the main terpenoids were detected in leaves of the 'Pilar' variety, slightly higher contents of the terpenoids α-pinene, β-pinene, terpinolene, and farnesene were detected in the inflorescences of the 'Divina' variety, although no significant differences were found in total terpenoid contents in inflorescences.

CONCLUSIONS

Plants of the variety 'Divina' cultivated for their esthetic value could be eventually harvested and used as an herbal remedy without any potential risk of abuse, giving a consistent added value to this dual-purpose variety. Extensive exploitation of an ornamental variegated *Cannabis* variety as starting material could be potentially considered for obtaining essential oil and CBD-enriched extracts with deprived residues of chlorophyll, as well as pure forms of CBD, especially when production of vegetable raw material take place in countries with restrictive rules on exploiting this plant species and where a morphological marker could make a difference on permitting its cultivation.

Literature Cited

Casano, S. (2019). Development of ornamental *Cannabis sativa* L. cultivars: phytochemical, morphological, genetic characterization and propagation aspects. Acta Horticulturae, 1263, 283-290 https://doi.org/10.17660/ActaHortic.2019.1263.37.

Codesido, V., Marín, M., Sánchez-Carnerero Callado, C., Ferreiro-Vera, C., and Casano, S. (2020). Cannabinoids and terpenoids yields of the ornamental *Cannabis sativa* L. cultivar 'Divina' characterized by a variegated foliage as morphological marker. Acta Horticulturae, 1287, 161-168 https://doi.org/10.17660/ActaHortic.2020.1287.21.

Lata, H., Chandra, S., Khan, I. A., Elsohly, M. A. (2017). Micropropagation of *Cannabis sativa* L.—An Update. In *Cannabis sativa* L.—Botany and Biotechnology. S. Chandra, H. Lata, and M. A. ElSohly, eds. (Oxford, Miss.: Springer International Publishing), p. 285-297 https://doi.org/10.1007/978-3-319-54564-6_13. PubMed Lichtenthaler, H. K. (1987). Chlorophylls and Carotenoids: Pigments of Photosynthetic Biomembranes. Methods in Enzymology 148, 350-382 https://doi.org/10.1016/0076-6879(87)48036-1. PubMed Potter, D. (2009). The propagation, characterisation and optimisation of *Cannabis sativa* L. as a phytopharmaceutical. Thesis for the degree of Doctor of Philosophy (PhD) in Pharmaceutical Sciences, Department of Pharmaceutical Science Research, King's College London, March 2009.

Potter, D. (2013). A review of the cultivation and processing of *Cannabis* (*Cannabis sativa* L.) for production of prescription medicines in the UK. Drug testing and analysis. Special Issue: Cannabinoids part II: The current situation with cannabinoids 6, 31-38 https://10.1002/dta.1531. PubMed Small, E., and Cronquist, A. (1976). A practical and natural taxonomy for *Cannabis*. Taxon 25, 405-435 https://doi.org/10.2307/1220524. PubMed

DETAILED BOTANICAL DESCRIPTION

The following is a detailed botanical description of the new variety 'Divina'. The color codes referred to herein are from the Munsell Plant Tissue Color Book and Charts (SKU M50150). These observations on leaves and stem were done on a stock plant having approximately 12 weeks of age, meaning that since the rooted cutting has been potted, it has been maintained for 12 weeks under 18 hours/day of artificial lighting (400-600 μmol $m^{-2}s^{-1}$), and under controlled temperatures and relative humidity, and CO2 enriched up to 800 ppm. Observations on inflorescences and flowers were done on the plant of FIG. 3, the day it was harvested.

The plant:

*Type* (*life form and habitat*).—Herbaceous tap-rooted annual.

*Classification*.—Variety of *Cannabis sativa* L., varietal denomination 'Divina'.

Origin, form and growth characteristics:

*Origin*.—Spontaneous natural mutation of the variety *Cannabis sativa* L., varietal denomination 'Pilar' (CPVO Application number 2016/0115; granted with decision N° EU 50009 of 16 Jul. 2018).

*Propagation*.—The variety 'Divina' is propagated solely by asexual reproduction, e.g., in vivo rooting of cuttings or in vitro shoot micropropagation. However, female inflorescences of plants of the variety 'Divina' can produce viable seeds when pollinated from fertile pollen of other *Cannabis* varieties.

*Mature habit*.—Tap-rooted annual with an extensive fibrous root system, upright and much branched aerial portion of the plant. Natural height is very short and overall size varies from 0.9-1.1 m tall and 0.3-0.4 m wide across at the widest point. However, the growth form of all cloned individuals can be highly manipulated by systematic removal a terminal buds, inducing a greater branching habit than without removing terminal buds. The growth form can also be significatively manipulated in height and width of plants by changing the period of exposing cloned individuals under a "long day" artificial light regime (>18 hours/day of light) and the pedoclimatic conditions of cultivation.. Plants do not flower when exposed to >18 hours/day of light.

*Growth*.—Vigorous annual herb.

Foliage (leaves):

*Arrangement*.—Alternate.

*Form*.—Palmately compound, (3) 5 linear lanceolate leaflets with glandular hairs mainly on the upper surface.

*Size*.—Whole.

*Leaf*.—11-16 cm long (with petiole), and 5.5-12.5 cm wide (9.2 cm average width); middle (largest) leaflet 7-12 cm long (without petiole), and 1.8-2.8 cm wide.

*Margins*.—Coarsely serrate.

*Color*.—Upper side — Bi-colored: green (7.5 GY 3/4) and yellow (2.5 GY 8/4). Variegation pattern is not uniform throughout the entire plant, but it can be described as predominantly blotched, and including leaves or leaflets with irregular yellow streaks and/or spots.

*Color*.—Lower side — Bi-colored: green (5 GY 5/4) and yellow (2.5 GY 8/2); with lighter colors than in the upper side of the leaves. Variegation pattern resembles the observed one on the upper side.

*Veins*.—Lower side — pronounced mid-rib, with straight axial branches at about a 45° angle, toward distal end of the leaflet.

*Color*.—Yellow (2.5 GY 8/2).

*Petiole*.—Length 3.0-4.5 cm at maturity.

*Color*.—Yellow (2.5 GY 8/2) in the lower side; medium anthocyanin intensity, providing a reddish color (5R 4/6) in upper side.

*Stipules*.—Present at base of petiole, 0.4-0.7 cm long, bulbous bases, acuminate (tapering concave to apex). Pale green color (7.5GY 9/2).

*Aroma*.—A blend of *Citrus* fruits and *Pinus* needles.

Stem:

*Shape*.—Roughly circular, shallow ribbed, with diameter of 1.6-7.3 (4.6 cm average). Short internodes, 2.5-5 cm length (3.5 cm average). Medium pith-in cross section, 1.5-2.5 cm diameter at base.

*Color*.—Medium green (2.5 GY 7/8).

Inflorescence:

*Blooming habit*.—Elongated compound cymes or panicles, generally forming spikes from 0.2 m to 0.4 m in length, densely packed with individual small pistillate flowers subtended by small leaves, these with densely packed capitate (stalked) glandular trichomes.

*Aroma*.—A blend of *Citrus* fruits and *Pinus* needles.

Flowers:

*Corolla*.—Petals and calyx unified and collectively appressed to and surrounding the ovary.

*Color*.—Variegated green (7.5 GY 3/4) and yellow (2.5 GY 8/4).

*Diameter*.—Apical cyme has 4-6 cm diameter.

*Shape*.—Elliptical.

*Involucral bracts*.—Present, several stalked glandular trichomes present only on its upper surface, enclose the flower. Typical length is 2.2-4.1 mm (3 mm average).

*Individual flower size*.—Pistillate flowers have a typical length of 7-12 mm (9.2 mm average) and 1.5-2.9 mm width (2 mm average).

*Calyces*.—Appressed to the base of the ovary with the corolla as a unified perianth.

*Color*.—Variegated green (7.5 GY 3/4) and yellow (2.5 GY 8/4).

*Filaments*.—N/A, no staminate flowers observed.

*Stigma*.—Length 5-7 mm, about 1 mm wide at base, tapering to distal end. Densely covered with q minute (<1 mm) hairs.

*Color*.—Lemony white (2.5 GY 8/2), drying slowly to orange (2.5 YR 5/8) from apex to base after anthesis.

*Number*.—2.

*Staminate column*.—N/A, no staminate flowers observed.

*Fruit*.—An achene in this genus; however, no fruits were seen in absence of viable pollen while fruits were seen in presence of viable pollen produced by other monoecious or dioecious male plants.

*Pollen*.—N/A, no staminate flowers observed; however, the artificial production of staminate flowers can be induced by applying silver thiosulphate (STS) to plants in vegetative stage or at the beginning of the flowering stage, meaning that the induced production of viable pollen can be artificially obtained.

*Petalage*.—The plant is essentially without petals (apetalous); these are fused and appressed to the base of the ovary with the calyx as the perianth.

*Pedicel*.—Flowers are essentially sessile (attached to the stem), and as such have no pedicel.

*Trichomes*.—Capitate (stalked) glandular trichomes are transparent or translucent before harvest, and sometimes showing a brownish dot inside. Once harvested, they become pale brown-amber.

General characteristics and culture:

*Blooming period*.—Plants will bloom in 4-6 weeks when 12 hours of light/day are applied to induce flowering.

*Hardiness*.—Probably it is fairly hardy; however, hardiness in nature is unknown as this plant has only been cultivated under controlled conditions.

*Breaking action*.—Stems are fibrous, strong and flexible, highly resistant to breakage.

*Rooting*.—Approximately 70% success rate with cuttings. After exposing for 2 minutes the basal part of the cuttings to a rooting solution containing natural auxins, treated cuttings were placed in peat cubes. The ranges adopted for climatic parameters were: 22±1° C., 75-85% of relative humidity, 350-400 ppm of carbon dioxide, and under a photon flux density of approximately 100 μE mol $m^{-2}s^{-1}$ provided by light-emitting diodes (LEDs) lights under continuous day-length (24 hours light/day). 'Divina' is susceptible to fungal disease during in vitro rooting.

*Growth regulator*.—No growth regulators or hormones were used in the cultivation stages, while in the propagation stage a liquid rooting product containing natural phytohormones was used for stimulating the formation of root primordia and their elongation.

*Shipping tolerance*.—The plant has been successfully shipped at controlled temperature (20° C.) by using Clone Shipper, which is a closed shipping container provided by a LED light to keep the plant in the vegetative stage while being shipped for 3-4 days before arriving to its destination.

*Shipping quality*.—Not known.

*Storage life*.—Not known.

*Market use*.—Ornamental use (potted plants) — medicinal use (fresh and dried leaves and inflorescences, or derived resins and extracts).

*Productivity*.—Average total fresh weight: 404.5 g per plant; average total dry weight: 81.58 g per plant; average dry weight of flowers: 19.55% of the plant total dry weight; average dry weight of leaves: 60.55% of the plant total dry weight; average dry weight of stems: 19.9% of the plant total dry weight.

It is claimed:

1. A new and distinct variety of a *Cannabis sativa* L. plant named 'Divina', as shown and described, characterized by a variegated yellow and green foliage.

* * * * *